US008858884B2

(12) United States Patent
Franciskovich et al.

(10) Patent No.: US 8,858,884 B2
(45) Date of Patent: Oct. 14, 2014

(54) COUPLED ENZYME-BASED METHOD FOR ELECTRONIC MONITORING OF BIOLOGICAL INDICATOR

(71) Applicant: American Sterilizer Company, Mentor, OH (US)

(72) Inventors: Phillip P. Franciskovich, Concord, OH (US); Tricia A. Cregger, Fairlawn, OH (US)

(73) Assignee: American Sterilizer Company, Mentor, OH (US)

( * ) Notice: Subject to any disclaimer, the term of this patent is extended or adjusted under 35 U.S.C. 154(b) by 0 days.

(21) Appl. No.: 13/832,158

(22) Filed: Mar. 15, 2013

(65) Prior Publication Data

US 2014/0273054 A1    Sep. 18, 2014

(51) Int. Cl.
*G01N 27/00* (2006.01)
*C12Q 1/22* (2006.01)
*C12Q 1/00* (2006.01)
*G01N 27/327* (2006.01)

(52) U.S. Cl.
CPC ..... *C12Q 1/22* (2013.01); *C12Q 1/006* (2013.01); *C12Q 1/001* (2013.01); *G01N 27/327* (2013.01)
USPC ......... 422/82.01; 422/52; 422/73; 422/82.05; 422/82.08; 422/82.09; 422/82.11; 422/400; 422/401; 422/420; 422/421; 422/422; 422/423; 422/424; 422/425; 422/426; 422/427; 422/428; 422/429; 422/68.1; 422/82.06; 422/407; 422/501; 422/502; 422/503; 422/504; 436/164; 436/177; 436/63; 436/43; 435/29; 435/4; 435/7.1

(58) Field of Classification Search
CPC ....... G01N 27/327; C12Q 1/006; C12Q 1/001
USPC ............. 422/82.01, 82.02, 82.03, 82.04, 401, 422/405, 547, 549, 550, 552, 558, 559, 560, 422/561, 52, 73, 82.05, 82.08, 82.09, 82.11, 422/99, 102, 400, 420, 421, 422, 423, 424, 422/425, 426, 427, 428, 429, 68.1, 82.06, 422/407, 501, 502, 503, 504; 436/1, 149, 436/150, 151, 152, 153, 807, 808, 809, 810, 436/164, 177, 43, 63; 435/29, 31, 287.4, 435/287.6, 288.1, 288.2, 4, 6, 7.1
See application file for complete search history.

(56) References Cited

U.S. PATENT DOCUMENTS 4,927,516 A    5/1990    Yamaguchi et al.
5,413,690 A    5/1995    Kost et al.

(Continued)

FOREIGN PATENT DOCUMENTS

WO    0210708    2/2002
WO    2008082728    7/2008
WO    2012012055    1/2012

OTHER PUBLICATIONS

Albert et al, "Biological indicators for steam sterilization: characterization of a rapid biological indicator utilizing *Bacillus stearothermophilus* spore-associated alpha-glucosidase enzyme" Journal of Applied Microbiology 1998, 85, 865-874).*

(Continued)

*Primary Examiner* — Dennis M White
(74) *Attorney, Agent, or Firm* — Renner, Otto, Boisselle & Sklar, LLP

(57) ABSTRACT

A sterilization indicator system and method of using the system to determine efficacy of a sterilization process. The system includes a vial having a first compartment containing spores of one or more species of microorganism; a second compartment containing a growth medium with a disaccharide, an oligosaccharide or a polysaccharide in which the vial is free of monosaccharide; an enzyme, capable of acting upon the monosaccharide to yield reaction products and electron transfer, disposed on two or more electrodes adapted to carry an electrical signal resulting from the electron transfer, the pair of electrodes positioned to contact the combined contents of the first compartment and the second compartment during incubation; and an apparatus linked or linkable to the electrodes and adapted to detect and measure the electrical signal resulting from electron transfer when the enzyme acts upon the monosaccharide.

18 Claims, 6 Drawing Sheets

(56) References Cited

U.S. PATENT DOCUMENTS

| | | |
|---|---|---|
| 5,789,255 A | 8/1998 | Yu |
| 5,843,692 A | 12/1998 | Phillips et al. |
| 5,902,731 A | 5/1999 | Ouyang et al. |
| 6,077,660 A | 6/2000 | Wong et al. |
| 6,102,872 A | 8/2000 | Doneen et al. |
| 6,168,957 B1 | 1/2001 | Matzinger et al. |
| 6,193,873 B1 | 2/2001 | Ohara et al. |
| 6,268,162 B1 | 7/2001 | Phillips et al. |
| 6,270,637 B1 | 8/2001 | Crismore et al. |
| 6,338,790 B1 | 1/2002 | Feldman et al. |
| 6,531,322 B1 | 3/2003 | Jurik et al. |
| 6,555,061 B1 | 4/2003 | Leong et al. |
| 6,562,625 B2 | 5/2003 | Modzelewski et al. |
| 6,572,822 B2 | 6/2003 | Jurik et al. |
| 6,716,577 B1 | 4/2004 | Yu et al. |
| 6,723,500 B2 | 4/2004 | Yu |
| 6,818,180 B2 | 11/2004 | Douglas et al. |
| 6,855,243 B2 | 2/2005 | Khan |
| 6,858,401 B2 | 2/2005 | Phillips et al. |
| 6,881,551 B2 | 4/2005 | Heller et al. |
| 6,989,243 B2 | 1/2006 | Yani et al. |
| 6,990,367 B2 | 1/2006 | Kiser et al. |
| 6,998,248 B2 | 2/2006 | Yani et al. |
| 7,226,978 B2 | 6/2007 | Tapsak et al. |
| 7,244,394 B2 | 7/2007 | Carney et al. |
| 7,288,174 B2 | 10/2007 | Cui et al. |
| 7,429,462 B2 | 9/2008 | Morris et al. |
| 7,548,772 B2 | 6/2009 | Shartle et al. |
| 7,549,323 B2 | 6/2009 | Charlton et al. |
| 7,653,492 B2 | 1/2010 | Davies et al. |
| 7,655,119 B2 | 2/2010 | Davies |
| 7,711,402 B2 | 5/2010 | Shults et al. |
| 7,731,835 B2 | 6/2010 | Buck et al. |
| 7,740,801 B2 | 6/2010 | Saini et al. |
| 7,835,777 B2 | 11/2010 | Shults et al. |
| 7,860,545 B2 | 12/2010 | Shults et al. |
| 7,875,461 B2 | 1/2011 | Docherty et al. |
| 7,888,292 B2 | 2/2011 | Bock et al. |
| 7,909,984 B2 | 3/2011 | Heller et al. |
| 7,922,985 B2 | 4/2011 | Mahoney et al. |
| 7,943,022 B2 | 5/2011 | Teodorczyk et al. |
| 7,964,372 B2 | 6/2011 | Marfurt |
| 7,964,390 B2 | 6/2011 | Rozakis et al. |
| 7,974,672 B2 | 7/2011 | Shults et al. |
| RE42,953 E | 11/2011 | Crismore et al. |
| 8,105,244 B2 | 1/2012 | Ghesquiere et al. |
| 8,133,178 B2 | 3/2012 | Brauker et al. |
| 8,142,642 B2 | 3/2012 | Heller et al. |
| 8,155,723 B2 | 4/2012 | Shults et al. |
| 8,178,313 B2 | 5/2012 | Mahoney et al. |
| 8,182,671 B2 | 5/2012 | Feldman et al. |
| 2004/0028557 A1 | 2/2004 | Leong et al. |
| 2007/0003995 A1* | 1/2007 | Song et al. ............... 435/31 |
| 2007/0208243 A1 | 9/2007 | Gabriel et al. |
| 2007/0212266 A1* | 9/2007 | Johnston et al. ............ 422/99 |
| 2008/0057528 A1 | 3/2008 | Sayre et al. |
| 2008/0177166 A1 | 7/2008 | Pronovost et al. |
| 2008/0281178 A1 | 11/2008 | Chuang et al. |
| 2009/0184004 A1 | 7/2009 | Chatelier et al. |
| 2009/0257911 A1* | 10/2009 | Thomas et al. ............. 422/22 |
| 2009/0270704 A1 | 10/2009 | Peyser et al. |
| 2010/0126884 A1 | 5/2010 | Wang et al. |
| 2010/0204559 A1 | 8/2010 | Shults et al. |
| 2010/0216175 A1 | 8/2010 | Melker et al. |
| 2010/0259747 A1 | 10/2010 | Sekimoto |
| 2010/0270152 A1 | 10/2010 | Cardosi et al. |
| 2010/0273249 A1 | 10/2010 | Cardosi et al. |
| 2010/0298679 A1 | 11/2010 | Wu et al. |
| 2011/0040163 A1 | 2/2011 | Telson et al. |
| 2011/0048972 A1 | 3/2011 | Moffat et al. |
| 2011/0155585 A1 | 6/2011 | Chatelier et al. |
| 2011/0281287 A1 | 11/2011 | Marfurt |
| 2011/0290668 A1 | 12/2011 | Moffat et al. |
| 2011/0309846 A1 | 12/2011 | Elder et al. |
| 2011/0311711 A1 | 12/2011 | Say et al. |
| 2011/0319734 A1 | 12/2011 | Gottlieb et al. |
| 2012/0037514 A1 | 2/2012 | Wu et al. |
| 2012/0043204 A1 | 2/2012 | Young et al. |
| 2012/0073986 A1 | 3/2012 | Jackson et al. |
| 2012/0097554 A1 | 4/2012 | Shah et al. |

OTHER PUBLICATIONS

PCT/US2014/017907; PCT International Search Report and Written Opinion of the International Searching Authority dated Jun. 2, 2014.

* cited by examiner

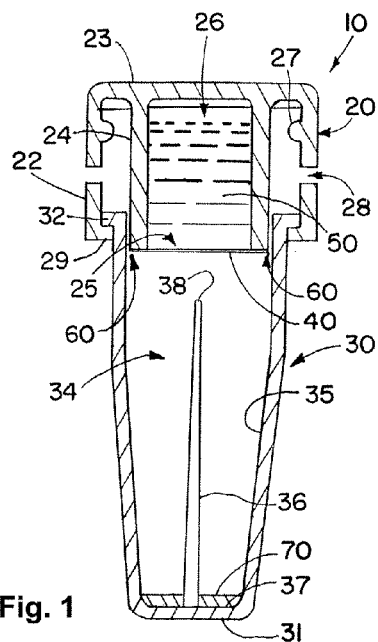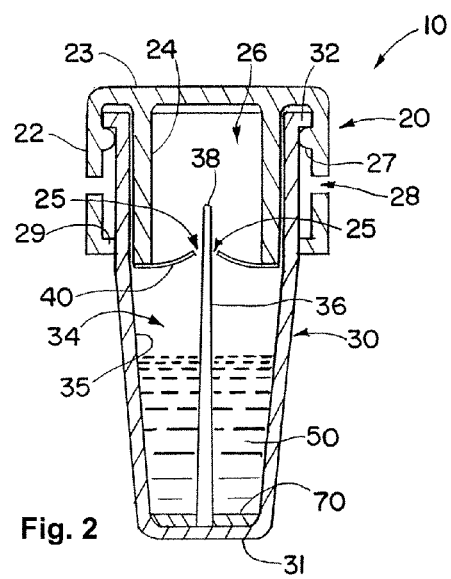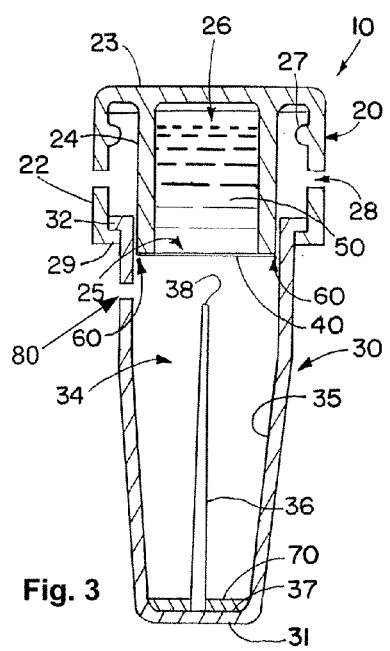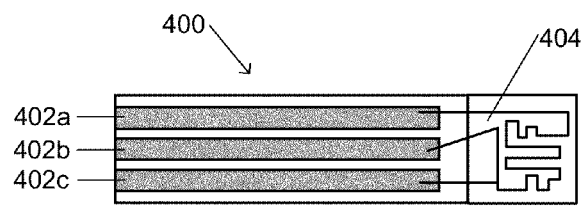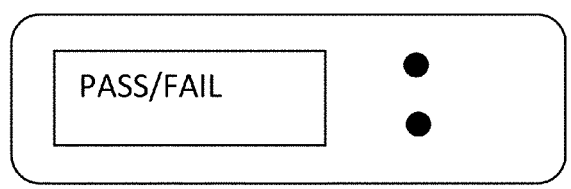

COUPLED ENZYME-BASED METHOD FOR ELECTRONIC MONITORING OF BIOLOGICAL INDICATOR

TECHNICAL FIELD

The present invention relates to biological indicators for testing the efficacy of sterilization processes, more specifically, to coupled enzyme-based methods for monitoring such biological indicators, in which such monitoring can be carried out electronically.

BACKGROUND

One of the most important classes of indicators are the biological indicators (BI). Biological indicators provide the highest degree of assurance that sterilization conditions were met within the processor or processed load itself. This type of indicator is meant to represent the worst case for the processing system by providing an extremely high number of highly resistant organisms to that particular process within or on the indicator. Usually bacterial spores are the organism of choice for monitoring sterilization systems.

Biological indicators typically consist of microorganisms inoculated onto a carrier material. The microorganisms are typically bacterial spores that are known to be very resistant to the particular sterilization medium in which they are to be used. The carrier is placed into a sterilization cycle along with the medical device load. Following completion of the cycle the biological indicator is incubated and monitored for growth for up to seven days. Growth of a biological indicator indicates that the sterilization process was not adequate to attain complete sterilization and that the medical device load needs to be reprocessed before use. No growth of a biological indicator confirms that conditions within the sterilizer were adequate to kill at least the number of bacterial spores loaded onto the indicator (e.g., $10^6$ bacterial spores) and therefore provides a level of assurance that the medical device load is sterile. Unfortunately many medical devices are actually used prior to the user knowing the results of the full incubation. Thus, there is a need in the hospital setting for detection of viable, germinating biological indicator spores in the shortest possible time.

Historically, the detection of viable biological indicators relied on visual means of detection. The growth and multiplication of viable organisms can be seen/detected as evidenced by turbidity in the growth media. This turbidity can take days to become noticeable. Another visual and more common means of detection is with a colorimetric pH indicator. As viable organisms begin to metabolize and use up the nutrient sources such as sugars that are provided in the growth media, they excrete acidic waste products. As these acidic waste products accumulate in the growth media, the pH of the system is lowered resulting in a color change of the growth media if a pH indicator is present. Detection by this means usually takes 18-48 hours.

More recently, fluorescence has been used to detect the activity of enzymes that are produced by the organisms of interest by adding a fluorogenic enzymatic substrate to the growth media. This newer methodology lessens the incubation time from days to hours. However, the main limitation for reducing the incubation time beyond that seen for the fluorescence methodology is the inherent background fluorescence that naturally occurs with many components of the biological indicator including the plastic vials and growth media. Authentic, detectable signals must be high enough to be distinguishable over this inherent native background fluorescence. Therefore to increase the sensitivity of the system one needs to either reduce the background fluorescence (noise) or move to a different technology that has higher sensitivity (signal).

Thus, in the prior and current art, biological indicators rely on colorimetric or fluorometric means to determine viability. Detection is limited by the need for the generated signals, whether colorimetric or fluorometric, to be above substantial background levels. This has resulted in detection times for viable organisms on the order of hours to days in order for sufficient signal to be accumulated to be detectable above background levels. It would be beneficial for both hospitals and patients for the detection time of viable organisms in biological indicators to be on the order of minutes or less.

SUMMARY

One such method that permits control over the signal to noise ratio is electrical detection. The monitoring of changes in the electrical properties of systems is a sensitive means to monitor for other changes within that system. The resulting electric outputs can then be conditioned by appropriate electronic circuitry to provide amplified and filtered signals that are directly proportional to the reagent generating them.

The present invention provides a rapid detection of viable microorganisms of a biological indicator using a coupled enzyme-based electronic detection method to detect the accumulation of simple sugars (monosaccharides) such as glucose resulting from the enzymatic breakdown of complex sugars (disaccharides, oligosaccharides and/or polysaccharides). It is noted that the term "sugar" is used herein interchangeably with "saccharide". The coupled enzyme-based system of the present invention includes a combination of at least one naturally occurring glycosidase present in a viable spore and one oxidase; or the combination of at least one naturally occurring glycosidase present in a viable spore and one dehydrogenase. The incubation or growth medium provided for the spores post-sterilization is with a complex sugar, such as a disaccharide, a oligosaccharide and/or a polysaccharide, but free of a simple sugar. The glycosidase reacts with the complex sugar added to the growth media and breaks it down into the simple sugars, including, for example, at least one glucose. The simple sugar product is acted on by either an oxidase or dehydrogenase which produces an electron transfer as part of its action on the simple sugar. The quantity of the electron transfer is proportional to the amount of the simple sugar produced by viable spores. The transfer of free electrons can be monitored and measured electronically. If the electronic monitoring detects electron transfer, it means that at least some spores are viable and have survived the sterilization process, and so showing the sterilization was not efficacious. The enzyme may be one used in standard, state of the art blood glucose monitoring devices, and in fact, known state of the art blood glucose monitoring devices can be readily adapted for use in determining the presence of any glucose or simple sugar in the combined media. Thus, the present invention allows the determination of the efficacy of the sterilization process by a very specific, very sensitive method that can be simply carried out and measured electronically, using standard, state of the art devices designed for use in monitoring blood glucose levels in diabetic patients.

Thus, in one embodiment, the present invention relates to a sterilization indicator system, including:
  a vial including:
    a first compartment including spores of one or more species of microorganism;

a second compartment including a growth medium that includes one or more of a disaccharide, oligosaccharide or a polysaccharide capable of conversion to a monosaccharide by germinating cells of the one or more species of microorganism, and wherein the vial is free of the monosaccharide and is adapted to combine contents of the first compartment with contents of the second compartment for incubation after the vial has been exposed to a sterilant;

an enzyme, capable of acting upon the monosaccharide and producing an electron transfer, disposed on at least two electrodes adapted to carry an electrical signal resulting from electron transfer when the enzyme acts upon the monosaccharide, wherein the at least two electrodes are positioned to contact the combined contents of the first compartment and the second compartment during and/or after incubation; and an apparatus linked or linkable to the at least two electrodes and adapted to detect and measure the electrical signal resulting from electron transfer when the enzyme acts upon the monosaccharide.

In one embodiment, the one or more species of microorganism comprises one or both of *Geobacillus stearothermophilus* and *Bacillus atrophaeus*.

In one embodiment, the disaccharide is maltose and the monosaccharide is glucose.

In one embodiment, the disaccharide is maltose that is converted to glucose by a glucosidase produced by or present in the germinating cells during incubation of the combined contents of the first compartment and the second compartment.

In one embodiment, the enzyme is provided together with one or more mediator. In one embodiment, the one or more mediator comprises one or a mixture of two or more of ferrocene, vinyl ferrocene, 1,1'-dimethyl ferrocene, carboxyferrocene, 1,1'-dicarboxy ferrocene, (dimethylamino)methyl ferrocene or ferrocyanide.

In one embodiment, the at least two electrodes comprise graphite, graphene, carbon, carbon nanotubes, gold, platinum, palladium, silver, nickel or copper or a combination or alloy of any two or more thereof.

In one embodiment, the enzyme is glucose oxidase.

In one embodiment, the enzyme is glucose dehydrogenase.

In another embodiment, the present invention relates to a method for determining the efficacy of a sterilization process, including:

providing the sterilization indicator system as described above;

exposing the sterilization indicator to a sterilization process intended to kill the spores of the one or more species of microorganism;

combining the contents of the first compartment and the second compartment;

exposing the combined contents to the enzyme disposed on the two or more electrodes while incubating the combined contents;

with the apparatus linked to the electrodes, detecting and measuring any electrical signal resulting from the electron transfer when the enzyme acts upon the monosaccharide; and determining whether the sterilization process was efficacious.

Thus, the present invention provides an elegant and simple solution to the problem of rapidly determining the efficacy of a sterilization process, and provides an apparatus adapted for such use.

BRIEF DESCRIPTION OF THE DRAWINGS

The present invention may be useful with a variety of sterilization indicator apparatus. The annexed drawings are intended to provide an exemplary, non-limiting depiction of a suitable sterilization apparatus and to demonstrate the disclosed process, for the purpose of providing a better understanding of the invention, and are not intended to be limiting in any way. In the annexed drawings, like parts and features may have like references.

FIG. 1 is a schematic cross-sectional view of a first embodiment of a sterilization indicator suitable for use with embodiments of the present invention, in a pre-activated configuration.

FIG. 2 is a schematic cross-sectional view of the sterilization indicator of FIG. 1 in an activated configuration.

FIG. 3 is a schematic cross-sectional view of a second embodiment of a sterilization indicator suitable for use with embodiments of the present invention, in pre-activated configuration, similar to that of FIG. 1.

FIG. 4 is a schematic depiction of an electro-conductive strip containing three electrodes suitable for use in an embodiment of the present invention.

FIG. 5 is a schematic depiction of a test incubator/reader for use in an embodiment of the present invention.

Figure 6:
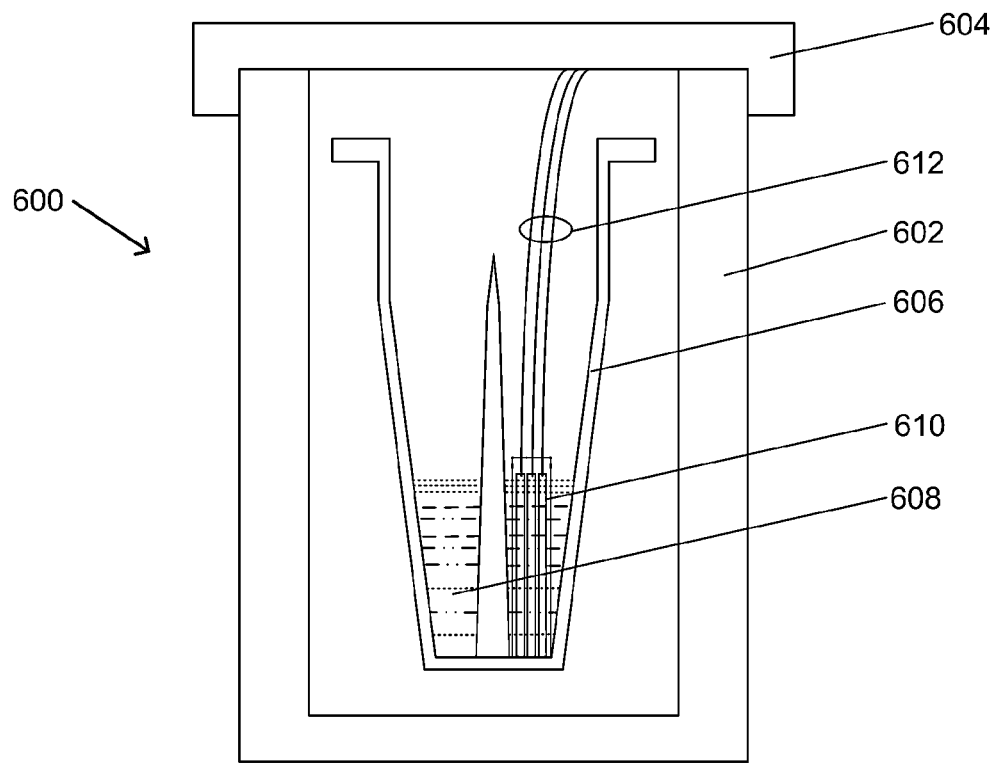
FIG. 6 is a schematic cross-sectional view of an embodiment of a sterilization indicator during incubation with an electro-conductive strip similar to that of FIG. 4 inserted into the combined contents of the first and second compartments, in test incubator/reader in accordance with the present invention.

It should be appreciated that for simplicity and clarity of illustration, elements shown in the Figures have not necessarily been drawn to scale. For example, the dimensions of some of the elements may be exaggerated relative to each other for clarity. Further, where considered appropriate, reference numerals have been repeated among the Figures to indicate corresponding elements.

Furthermore, it should be appreciated that the process steps and structures described below may not form a complete process flow for producing an end-useable sterilization indicator. The present invention can be practiced in conjunction with apparatus and processing techniques currently used in the art, and only so much of the commonly practiced process steps are included as are necessary for an understanding of the present invention.

DETAILED DESCRIPTION

The biological indicators presently described rely on a different mechanism to detect spore viability. The invention described here utilizes an electronic signal that is generated based on the accumulation of the simple sugar glucose resulting from the ability of viable organisms to breakdown complex sugars. Electronic detection methods based on sugars have been readily available for years for monitoring the glucose levels in the blood of diabetic patients. Until now, however, these electronic detection mechanisms have not been used as a means to detect viable organisms following sterilization processes.

Most organisms have inherent capabilities to break complex sugars (such as maltose) into simple sugars (such as glucose) in order that the more useful simple sugar, e.g., glucose, molecule can be utilized as an energy source by the organism. Glucose monitoring through electronic detection methods has been readily available for years to monitor the glucose levels in the blood of diabetic patients. The same basic reactions utilized in monitoring glucose levels in blood can be adapted to detect viable organisms, such as spores, that may survive a sterilization cycle, in the present invention, the same electronic glucose monitors may be adapted for use in monitoring efficacy of sterilization processes. Unlike blood glucose monitoring, where glucose is prevalent and measured directly, in the present invention glucose is obtained from an undetectable complex carbohydrate molecule that must first be acted upon by a viable organism before glucose is released and able to be detected. Thus, in the present invention, the simple sugar, usually glucose, is never present unless and until a viable microorganism that has survived the sterilization conditions being monitored breaks down a complex carbohydrate to form the simple sugar. IN addition, the relevant concentrations of glucose or other simple sugar are expected to be much lower in the combined media of the present invention than in blood glucose determinations. Whereas blood glucose generally has a concentration in the range from about 2 mM to about 30 mM, the present invention is capable of detecting simple sugar concentrations ranging from just above the minimum detection limits of the device up to the same glucose concentrations as found in blood. However, in a sterilization indicator, post-sterilization, almost all of the spores are expected to be killed and so the concentration of the simple sugars, if any, are expected to be and are in the range from just above the minimum detection limits of the device up to 0.1 mM, and in another embodiment, up to about 0.01 mM, and in another embodiment, up to about 0.001 mM.

As viable spores begin to germinate (a fundamental life activity) they produce and release enzymes that enable them to break down the complex sugars into more readily usable simple sugars such as glucose. By formulating a medium that is high in complex sugars (selected on the basis that they can be broken down by the active enzymes of surviving, germinating test organisms selected for the sterilization indicator) an increase in simple sugar, e.g., glucose, would be expected upon exposing viable spores to this medium and this increasing concentration of the simple sugar in the growth media can be detected when in the presence of a second enzyme, such as glucose oxidase or glucose dehydrogenase. Under the conditions of sterilization, all spores are intended to be killed and any enzymes the spores may already possess also will be destroyed. Therefore, an increase in the simple sugar detected after exposure of these spores to the medium of this invention confirms that the organisms are viable and germinating (proof of life). The spore mediated conversion of complex sugars to simple sugars represents the first step in the coupled enzyme process of the present invention.

The organisms of most interest for monitoring sterilization processes are *Geobacillus stearothermophilus* and *Bacillus atrophaeus*. *Geobacillus stearothermophilus* produces the enzyme alpha-glucosidase (for example) which breaks down the complex sugar maltose into two glucose molecules. This exemplifies just one means to achieve the first step in the coupled enzyme based system.

Then in the second step, the glucose can then be acted on by glucose oxidase (for example) which will then produce gluconic acid, hydrogen peroxide and free electrons. The free electrons produced by the enzyme are monitored electronically. A mediator can be added to expedite the transfer of electrons to an electrode, to further enhance the signal. This exemplifies just one means to achieve the second step in the coupled enzyme based system. In another embodiment, in the second step, the enzyme used is glucose dehydrogenase, which produces glucono-delta-lactone and NADH from glucose and NAD, which also involves an electron transfer that can be detected electronically.

Thus the second step in the process is dependent upon the first step in the process and is said to be coupled. Failure to achieve production of the end product of the first step (as will be the case if all the spores are killed) prevents initiation of the second step. So, in the absence of any product of the first reaction (e.g., glucose converted from maltose), no electrons can be transferred in the coupled second step and no signal will result or be observed, in this case, absence of any signal derived from electron transfer would mean the monitored sterilization was successful.

Examples of suitable disaccharides are maltose, lactose, sucrose, trehalose, cellobiose, and isomaltose Examples of suitable oligosaccharides are fructo-oligosaccharides, galacto-oligosaccharides, mannan-oligosaccharides, gum arabic, guar gum and guar hydrolysate.

Examples of suitable polysaccharides are starch, dextrin, glycogen, cellulose and pectin. Other possibly suitable polysaccharides include gellan, Gum ghatti, karaya, tragacanth, psyllium seed, xanthan, guar, ivory nut mannan, konjac, locust bean, tamarind, tara, carrageenans, alginates, fucoidans, laminarin, agar, pullulan, welan and scleroglucan.

Other suitable disaccharides, oligosaccharides and/or polysaccharides may be known to those of skill in the art, and may also be useful with the present invention.

The following exemplary reactions show the coupling of the enzyme naturally occurring in any germinating cells that survive the sterilization process and the enzyme added to the incubation/recovery medium (or pre-deposited onto the electrodes themselves) in accordance with an embodiment of the present invention:

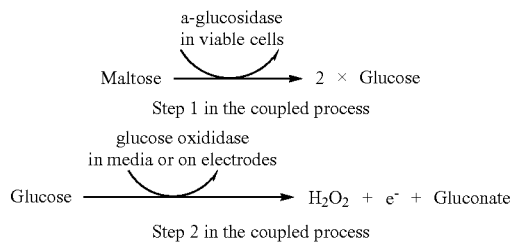

When a voltage differential is applied across a working electrode and a reference electrode, the working electrode becomes polarized and an oxidizing current resulting from the electron transfer is produced. This oxidizing current can be measured and is proportional to the amount of glucose present is the system. Thus, in the present invention, the electron transfer in the second step constitutes the current, if any, that is measured.

In one embodiment, the enzyme in the second coupled reaction is provided together with one or more mediator. In one embodiment, the one or more mediator comprises one or a mixture of two or more of ferrocene, vinyl ferrocene, 1,1'-dimethyl ferrocene, carboxyferrocene, 1,1'-dicarboxy ferrocene, (dimethylamino)methyl ferrocene, or a ferrocyanide. Other suitable mediators, such as those known in the blood glucose monitoring arts, can be used, as will be understood by the skilled person.

In one embodiment, the at least two electrodes comprise graphite, graphene, carbon, carbon nanotubes, gold, platinum, palladium, silver, nickel or copper or a combination or alloy of any two or more thereof. Other suitable electrode materials, as known in the blood glucose monitoring arts, can be used, as will be understood by the skilled person.

Referring now to the drawings, FIGS. 1 and 2 show a sterilization indicator system 10 useful with a first exemplary embodiment of the present invention. The indicator system 10 comprises a cap 20 that is mountable on a container 30. The container 30 includes a closed, bottom end 31 and an open, upper end, and defines an interior space 34. The cap 20 has an outer wall 22, an open, lower end, and a closed, upper end 23. The cap also includes an inner wall (or walls) 24 disposed interior of the cap's outer wall, forming a separate wall, and defining an inner chamber 26. The inner chamber 26 includes an opening 25 adjacent to the bottom end of the wall(s) 24. The chamber 26 contains a fluid 50, and the cap 20 includes a breakable barrier 40 disposed about the opening 25 of the chamber 26 to encapsulate the fluid 50 within the chamber 26.

In the embodiment illustrated in FIGS. 1 and 2, the indicator system is configured for the cap 20 to be mounted to the container 30 in a snap-fit relationship. In other embodiments, not shown, the indicator system may be configured for the cap to be mounted to the container in a threaded relationship in which the cap is engaged with the container by threads and the system is activated by rotating the cap with respect to the container, i.e., screwing the cap further onto the container. As shown in FIGS. 1 and 2, the container 30 includes an annular projection 32 forming a ridge or lip adjacent or near the upper end of the container. The cap 20 includes an annular projection 29 forming a ridge or lip adjacent the bottom of the cap. The cap 20 may be mounted onto the container 30 by sliding the ridge 29 of the cap over the ridge 32 of the container. The ridge 32 of the container 30 engages the ridge 29 on the cap 20 to prevent the cap 20 and container 30 from decoupling. The cap 20 and container 30 may be sized such that the ridge 32 exerts a sufficient amount of pressure against the cap 20 to prevent the cap 20 from sliding downward without applying an external downward force to the cap 20. In this way, the breakable barrier 40 may be kept spaced apart from the edges 38 of puncture members 36 so the breakable barrier 40 does not contact and/or is not broken by the puncture members until such time as desired to activate the indicator.

As shown in FIGS. 1 and 2, the container 30 is adapted to break the breakable barrier 40. The containers include one or more projections 36 (which may also be referred to herein as "puncture members") having an edge 38 adapted to break or puncture the breakable barrier 40 when the cap 20 with the breakable barrier 40 is moved downward toward and the barrier 40 contacts the edge 38 of projection 36. The puncture member 36 is shown as being integral with and extending up from the inner, bottom wall 37 of the container. In another embodiment, not shown, puncture members 36 may extend both from the side wall 35 and from the inner, bottom wall 37.

To evaluate a sterilization process, a calibrated concentration of microorganisms is disposed within the interior 34 of the container 30. The microorganisms may be disposed directly on the walls 35 of the container or may be provided on a support member (e.g., support member 70) that is disposed within the container 30. The sterilization indicator is then assembled by mounting the recovery medium-filled cap 20 on the container 30. The cap 20 may be mounted by snap-fitting the cap 20 onto the container 30 as described above, or, for example, by a threaded mounting. With reference to FIG. 1, the recovery medium-filled cap 20 is mounted on the container 30 in a first, non-activated (or open) position such that the breakable barrier 40 remains intact and is not punctured by the puncture members 36. Desirably, in the first, non-activated position, the breakable barrier 40 is positioned away from and does not contact the edges 38 of the puncture members 36.

With the indicator 10 assembled such as shown in FIG. 1, the sterilization indicator then can be subjected to a sterilization process. The cap 20 is shown as having apertures 28 through which a sterilant vapor may enter and flow into indicator system. The sterilant enters the cap through the apertures 28 (into the space between the outer wall 22 and the inner wall 24) and flows into the container 30 through a space 60 defined between the exterior surface of the inner wall 24 on the cap 20 and the inner surface of the wall 35 on the container 30. The sterilant vapor flows into the container 30 and acts upon the microorganisms of the biological indicator.

After the sterilization process is completed, the sterilization indicator may be activated by moving the cap 20 downward toward the container 30 to a second (or closed or activated) position, which is illustrated in FIG. 2. The cap 20 is moved downward by applying a sufficient downward force or pressure on the cap 20. As the cap 20 is moved downward, the breakable barrier 40 is brought into contact with the edge 38 of the puncture member 36, and eventually moved into a position such that the edge 38 of the puncture member 36 punctures or penetrates the breakable barrier 40. When the breakable barrier 40 is punctured, the opening 25 of the chamber 26 is exposed, and the liquid recovery medium 50 drains into the interior region 34 of the container 30 and into contact with the microorganisms as shown in FIG. 2.

As shown in FIGS. 1 and 2, in this embodiment, the inner surface of the cap 20 includes a second annular projection 27, and the cap may be moved downward to a position such that the upper portion of the projection 27 engages the bottom of ridge 32 on the container 30, and the cap 20 is held in the second, closed/activated position. The second, closed/activated position may serve to hold the cap 20 in a sealed relationship with the container 30, which may prevent additional microorganisms from entering the system.

It will be appreciated that, in another embodiment, the cap 20 does not include the second projection 27 to maintain the container in the closed position. In one alternative embodiment, the container 30 may include another annular projection or a set of detents (not shown) on the outside of the container 30 and located below the ridge 32, which projection or detents may be adapted to engage the ridge 29 on the cap to maintain the container 30 in a closed position. U.S. Pat. No. 5,770,393 illustrates such a configuration, and this patent is incorporated herein by reference for its teachings relating to configurations of cap and container. In another alternative embodiment, the inner surface of the cap 20 and the outer surface of the container 30 may be threaded, and the cap 20 may be moved into and maintained in a closed position by screwing the cap 20 onto the container 30, in which the cap 20 may be threaded as shown, e.g., in U.S. Pat. No. 8,173,388 B2, which may be consulted for additional details on this embodiment of the vial, and which is hereby incorporated herein by reference for its teachings relating to the vial and cap configuration of this and the foregoing embodiments. All of these alternative configurations are within the scope of the present invention.

As described above, the cap 20 in the embodiment illustrated in FIGS. 1 and 2 is shown as having the aperture 28 to allow for the ingress of the vapor sterilant into the indicator. It will be appreciated, however, that the cap need not be provided with such a feature. The number, size, shape, and/or location of the aperture(s) may be selected as desired, with consideration of the particular sterilant with which the sterilization indicator is to be used. For example, the location, shape, and size of the apertures in the cap and/or the container may be selected to provide a tortuous path for the entrance and exit of the sterilization vapor between the microorganisms and the surrounding environments. The tortuous path may also serve to inhibit or prevent contamination from external agents, and to make certain that an adequate amount of sterilant is available. By including the tortuous path, it is more likely that the entire load will be exposed to the sterilant thereby killing any extant microorganisms before the test organism in the sterilization indicator is killed.

Apertures may be provided in the container in addition to or as an alternative to providing apertures in the cap. If apertures are not provided in the cap, the inner wall(s) need not be located to provide a space between the inner wall of the cap and the inner surface of the container. Additionally, if apertures are provided in the container, they should be located such that the growth medium does not leak or spill out through such apertures when the indicator is activated and the barrier is broken.

FIG. 3 depicts an indicator 10 in which an aperture 80 is formed in the sidewall 35 of the container 30 at an appropriate position, in addition to the apertures 28 in the cap 20. The aperture shown in FIG. 3 is in the sidewall 35 of the container 30 be near the top of the container 30, in the vicinity of the edge 38 of the puncture member 36, to avoid leakage or spilling after activation. As can be seen from FIG. 3, after activation, the aperture 80 at this location will be covered by the cap 20 in the activated position. It is noted that the indicator 10 shown in FIG. 3 includes the aperture 28 in the cap 20, but this is not necessary. In one embodiment (not shown), the container 30 includes the aperture 80 and is used with a cap similar to the cap 20, but which does not include an aperture such as the aperture 28. Thus, an aperture can be provided either in the cap or in the container, or in both the cap and the container.

After the sterilization process has been completed, the cap 20 is pressed or twisted downward such that the edge 38 of the puncture member 36 penetrates and breaks the breakable barrier 40 releasing the growth medium in the space 26 to mix with and incubate with any of the biological indicator microorganisms that may have survived the sterilization process. The recovery medium 50 may comprise an aqueous medium or aqueous solution that provides for germination, metabolism and subsequent grow out of organisms as required. The aqueous medium or aqueous solution may be buffered.

The sterilization indicator 10 is then incubated for a sufficient period of time to allow microorganism viability to be determined. During incubation, any viable microorganisms will begin to germinate, and this germination includes activity by the enzymes to break down the disaccharide, oligosaccharide and/or polysaccharide to produce a monosaccharide, for example to break down maltose to produce glucose. In accordance with the present invention, the glucose "byproduct" is then available to be acted upon by the enzyme that is provided to act upon the glucose in the second step of the coupled enzyme system, which action includes an electron transfer, which electron transfer is detected via the electrical signal produced by the two or more electrodes described herein.

In one embodiment, the combined contents of the two compartments in the container, with the cap removed, are inserted into an incubator, as shown and described with respect to FIG. 6, which is discussed below, with an immobilized enzyme on the electrodes, as shown and described with respect to FIGS. 4 and 7, below, where the incubation and signal detection is carried out. In another embodiment, the combined contents are poured into a tray with the electrodes as shown and described with respect to FIGS. 4 and 7 at the bottom of the tray, where the incubation and signal detection take place. In the presently most preferred embodiment, the combined contents are introduced into a glucose detection device substantially similar, but with appropriate modifications, to those well known for use in monitoring glucose in blood.

FIG. 4 is a schematic depiction of an electro-conductive strip 400 containing three electrodes 402*a*, 402*b* and 402*c* suitable for use in an embodiment of the present invention. The strip 400 further includes electronics 404 adapted to provide electrical communication between the electrodes 402*a*, 402*b* and 402*c*, and an apparatus linked or linkable to the electrodes that is adapted to detect and measure the electrical signals resulting from electron transfer when any glucose present is acted upon by the enzymes on the electrodes. As disclosed and described, one or more of the electrodes 402*a*, 402*b* and 402*c* have attached an enzyme capable of acting upon a simple sugar, such as glucose, to produce a detectable electron transfer. As described, the at least two electrodes, may include two electrodes that participate in the electron transfer, while the third electrode may function as a reference electrode. Other embodiments, not shown, may include a different number of electrodes. For example, the reference electrode may be omitted, or an additional electrode or pair of electrodes may be added. The electronics 404 may include any appropriate electrical connection between the electrodes and an external apparatus that detects and measures any electrical signals generated. Such connections may include, but are not limited to, hard wiring (see, e.g., FIG. 6), physical electrical contacts, e.g., spring-loaded or jacks, Ethernet, Bluetooth, 802.11, wireless local area networks (WLANs), WiFi, WiMax and the like, or any other wired or wireless communication type known in the art.

FIG. 5 is a schematic depletion of a test incubator/reader for use in an embodiment of the present invention. The test incubator/reader may include electrical connections suitable to connect to the three electrodes described with respect to FIG. 4. The test incubator/reader may include heating and atmosphere controls to provide an appropriate temperature and atmosphere for incubation of the combined contents of the first compartment and the second compartment of the sterilization indicator. The test incubator/reader may further include electronic circuitry adapted to detect and measure any electrical signal generated when the enzyme provided on the electrodes converts a simple sugar, e.g., glucose, to reaction products including free electrons, in accordance with the present invention. FIG. 6 provides an example of a suitable arrangement for the test incubator/reader depicted in FIG. 5.

FIG. 6 is a highly schematic cross-sectional view of an exemplary sterilization indicator during incubation in an exemplary test incubator/reader 600, with the enzyme-immobilized electrodes in place. The test incubator/reader depicted in FIG. 6 includes a lower container 602 and a cap or lid 604. As shown in FIG. 6, disposed in the test incubator/reader 600 is a sterilization indicator vial 606, in which the recovery/ incubation medium 608 has been combined with test organisms, e.g., *Geobacillus stearothermophilus*, following a sterilization process which is being subjected to efficacy determination in accordance with an embodiment of the present invention. The test incubator/reader 600 is equipped with an electro-conductive strip 610, similar to that of FIG. 4, which has been inserted into the combined contents of the first and second compartments in the container 602, in the test incubator/reader 600 in accordance with an embodiment of the present invention. The test incubator/reader 600 further includes electrical connections 612 between the three electrodes on the strip 610 and the electrical circuitry used to detect any electrical activity generated by the enzymatic conversion of simple sugars to their reaction products. In the embodiment illustrated in FIG. 6, the conductive strip is hard-wired. In other embodiments, the conductive strip may communicate wirelessly as described with respect to FIG. 4.

Figure 7A:
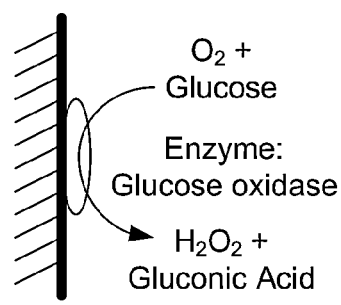
FIGS. 7a and 7b are reaction schemes showing immobilized enzymes on electrodes and an exemplary reaction of two enzymes on the simple sugar glucose.
Figure 7B:
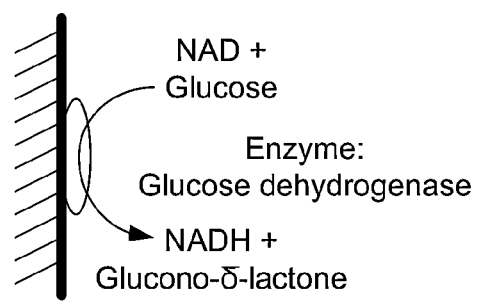

FIGS. 7a and 7b are reaction schemes showing an immobilized enzyme on an electrode and an exemplary reaction of two enzymes on the simple sugar glucose. In the embodiments of both FIGS. 7a and 7b, the appropriate enzyme is immobilized on the electrode. In the embodiment of FIG. 7a, the enzyme is glucose oxidase, and in the embodiment of FIG. 7b, the enzyme is glucose dehydrogenase. In both embodiments, the system is provided with appropriate co-reactants, e.g., oxygen and NAD, as shown. In both embodiments, action of the enzyme upon glucose (or in other embodiments, on the simple sugar) results in an electron transfer that can be detected electronically.

Figure 8:
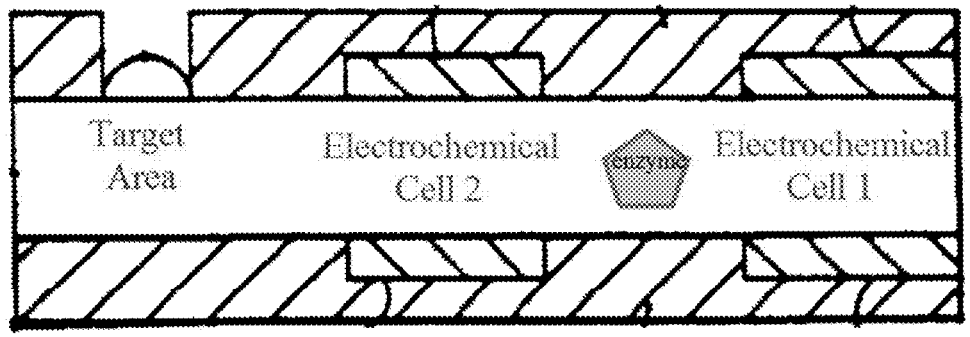
FIG. 8 is a schematic depiction of the layout of a glucose monitor device for use with embodiments of the present invention.

FIG. 8 is a schematic depiction of the layout of an exemplary test strip for a glucose monitoring device for use with embodiments of the present invention. The test strip includes a target area, a first electrochemical cell and a second electrochemical cell, with an enzyme shown between the electrochemical cells. The enzyme in the test strip of FIG. 8 would be the enzyme that acts on the simple sugar to effect an electron transfer that can be detected electronically as described herein. The test strip includes two sets of electrochemical cells. The cells may be positioned less than 500 µm apart. The cells include working electrodes and a counter/reference electrode. If a separate reference electrode is used from the counter electrode, it can be put in any suitable location. The second electrochemical cell zone is situated intermediate the first cell zone and the target area. The liquid containing the combined contents of the two compartments of the sterilization indicator comes into contact with the enzyme in, or en route to, the first electrochemical cell while the liquid reaching the second cell does not contact the enzyme. Potential is applied between both working electrodes and counter electrodes, and the change in current with time is measured separately for each pair. This allows the determination of the concentration of enzyme-induced electron transfer. Thus, the two cells are exposed to the same liquid, and thus control for interfering substances, except that the liquid in the second cell exhibits additional current flow if the simple sugar, e.g., glucose, was present in the combined contents and was acted upon by the enzyme. Subtraction of the one value for current flow from the other allows the determination of the concentration of the simple sugar in the combined contents of the two compartments of the sterilization indicator. If there is no difference, then there was no simple sugar present, and the sterilization is deemed successful. If there is a difference, then there was present the simple sugar and the sterilization is deemed unsuccessful.

Figure 9:
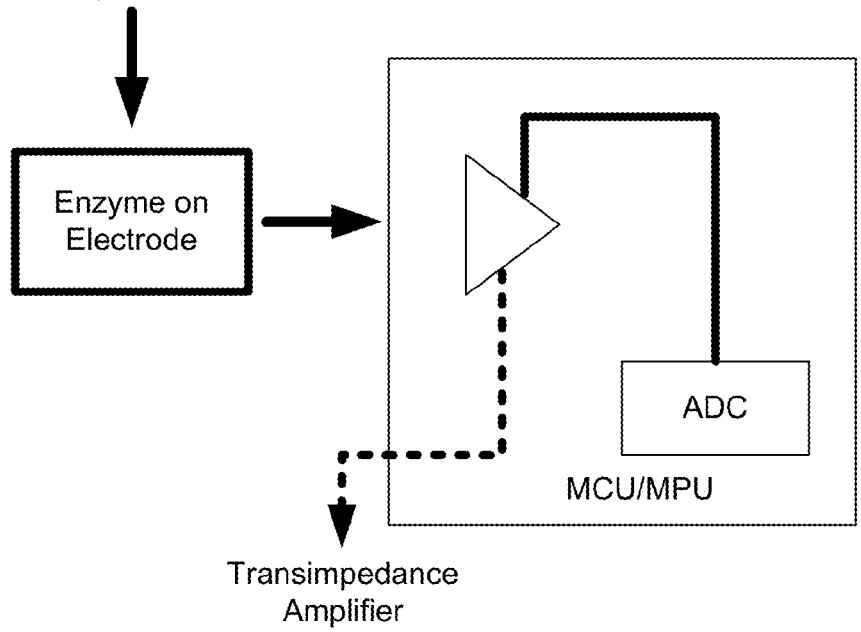
FIG. 9 is a schematic depiction of a device for receiving the signal produced by an enzyme on an electrode, converting it to a digital signal and transferring it to a microcontroller.

FIG. 9 is a schematic depiction of a device for receiving the signal produced by the reactive electrode, converting it to a digital signal and transferring it to a microcontroller. As will be understood by the skilled person, the differential signal obtained from the reactive electrode in the test strip, as modified and measured by the transimpedance amplifier, is fed to an analog digital converter (ADC) and then to the microcontroller/microprocessor unit (MCU/MPU), which in turn outputs the results to a display by which the user can determine the outcome of the test, and whether the sterilization was successful.

Example 1

Figure 10:
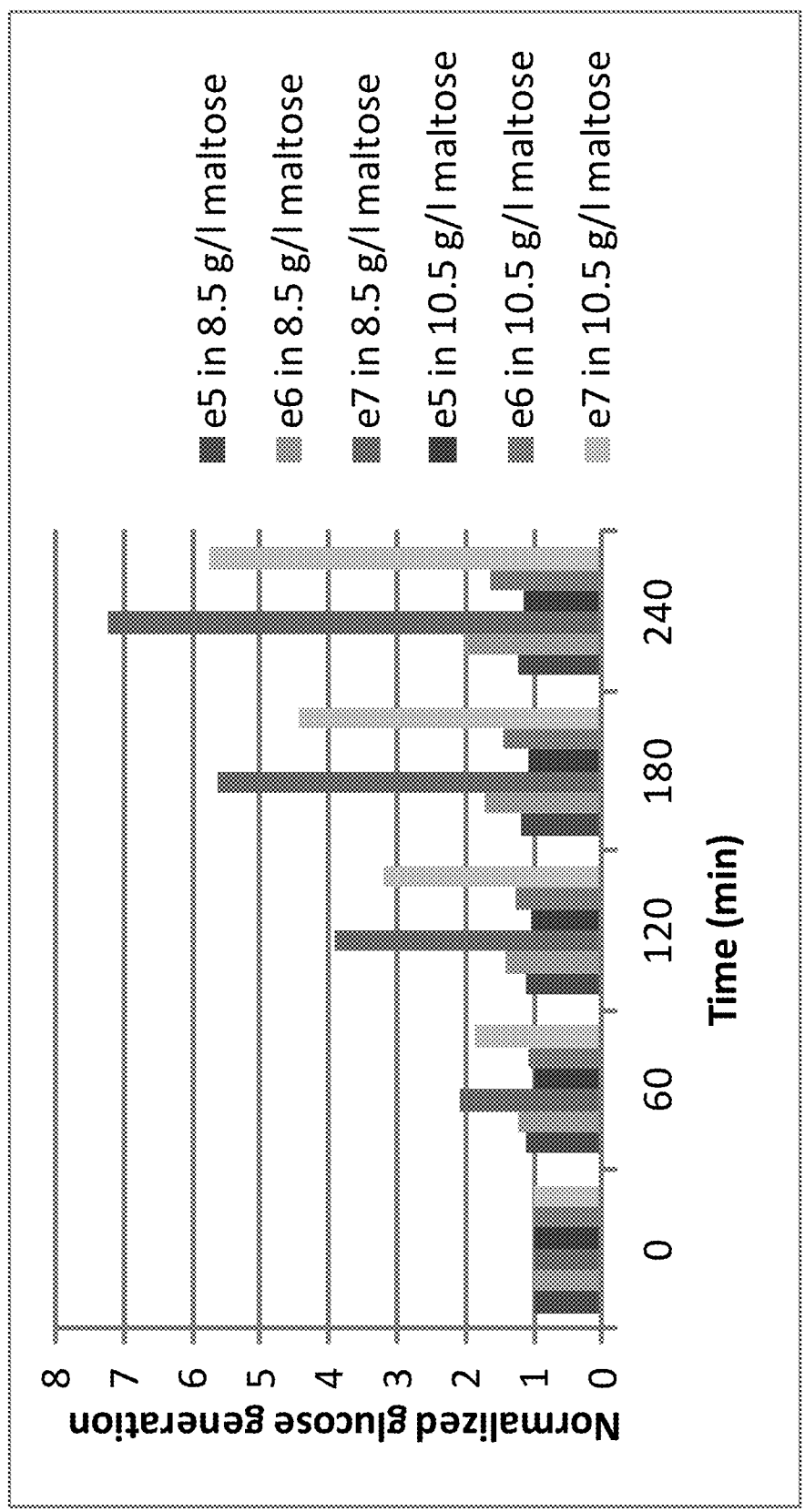
FIG. 10 is a bar graph which shows the effects of spore concentration and maltose concentration on the amount of glucose generated over time by an enzyme in a germinating spores of *Geobacillus stearothermophilus*.

Germinating spores of *Geobacillus stearothermophilus* at a population of E5, E6 and E7 spores per reaction containing growth media are monitored over several hours for illustrative purposes using a Biochemical Analyzer (YSI Instruments) using a glucose electrode. The growth media consists of glucose-free tryptic soy broth (TSB) at ⅛th the standard TSB concentration (to minimize interference from media components), containing the complex sugar maltose at concentrations of either 8.5 g/l or 10.5 g/l. Glucose measurements are taken every 60 minutes. All samples are normalized with respect to the initial glucose reading of the media. Observations are made over an extended time frame to measure the overall kinetics of the reaction for the selected conditions. The results are shown in FIG. 10, which shows the effects of the spore concentration and maltose concentration on the amount of glucose generated over time.

Example 2

Spores of *Geobacillus stearothermophilus* at populations of E5, E6, and E7 are evaluated for how rapidly the presence of viable organisms might be detected by levels of glucose produced as the viable germinating organisms from the spores break down the selected level of maltose into glucose in various formulations of media. The media are formulated with varying concentrations of glucose-free tryptic soy broth ranging from ⅛th of the standard glucose-free TSB (Tryptic soy broth) concentration to full standard concentration while keeping the maltose concentration constant at 8.5 g/l. Glucose-free TSB is a general nutrient source for bacteria and it contains pancreatic digest of casein, papaic digest of soybean, and salts and buffers; thus by diluting it we effectively reduce the amount of any interfering components present in the medium. The 'media only' samples are monitored throughout the study to see the effects of the various concentrations of TSB on the background signal. All samples are incubated at 56° C. for four hours with measurements being taken every 60 minutes. The growth media of the organisms is monitored using a Biochemical Analyzer (YSI instruments) and a glucose electrode.

Figure 11:
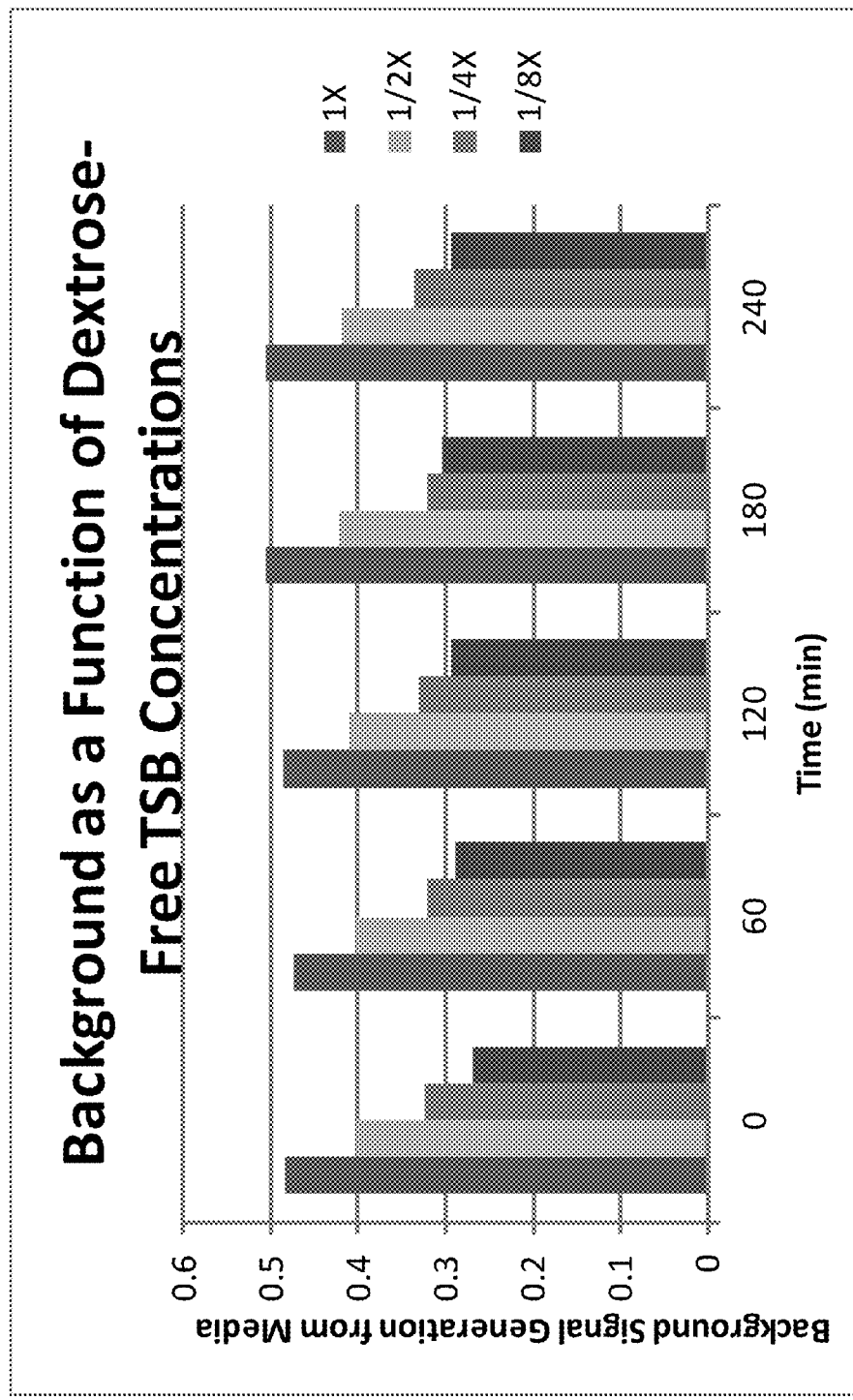
FIG. 11 is a graph which shows changes in the background signal measured over incubation periods for each of four glucose-free TSB concentrations without viable organisms present.

FIG. 11 shows the changes in the relative background signal measured over the incubation period for each of the four TSB concentrations without viable organisms present. The data demonstrates that the background signal is reduced at lower concentrations of TSB.

Table 1 below shows the tabulated normalized data measured in samples with viable *Geobacillus stearothermophilus*. The data is normalized against the respective media background for that incubation time. All values at or below the value of one are not distinguishable over the background. The normalized data demonstrates that the detection levels needed are reduced when the background signal is at its lowest. At a 1× glucose-free TSB concentration, a population of E5 spores cannot be detected within 4 hours whereas a population of E5 spores can be detected in 4 hours in a media formulated with ½× glucose-free TSB.

TABLE 1

Detection of glucose produced by viable spores of *Geobacillus stearothermophilus* incubated in various media

| Time  | 1X TSB | | | ½X TSB | | | ¼X TSB | | | ⅛X TSB | | |
|-------|--------|-------|-------|-------|-------|-------|-------|-------|-------|-------|-------|-------|
| (min) | E5 | E6 | E7 | E5 | E6 | E7 | E5 | E6 | E7 | E5 | E6 | E7 |
| 0   | 1     | 1     | 1     | 1     | 1     | 1     | 1     | 1     | 1     | 1     | 1     | 1     |
| 60  | 0.986 | 1.028 | 1.394 | 1     | 1.074 | 1.727 | 1     | 1.083 | 1.812 | 1.034 | 1.138 | 1.942 |
| 120 | 1     | 1.096 | 1.849 | 1.008 | 1.179 | 2.634 | 1.010 | 1.273 | 3.505 | 1.023 | 1.295 | 3.590 |
| 180 | 1     | 1.145 | 2.342 | 1.008 | 1.244 | 3.417 | 1.062 | 1.500 | 5.219 | 1.066 | 1.527 | 5.022 |
| 240 | 0.987 | 1.224 | 2.816 | 1.016 | 1.333 | 4.087 | 1.059 | 1.673 | 6.168 | 1.136 | 1.841 | 6.659 |

Example 3

Figure 12:
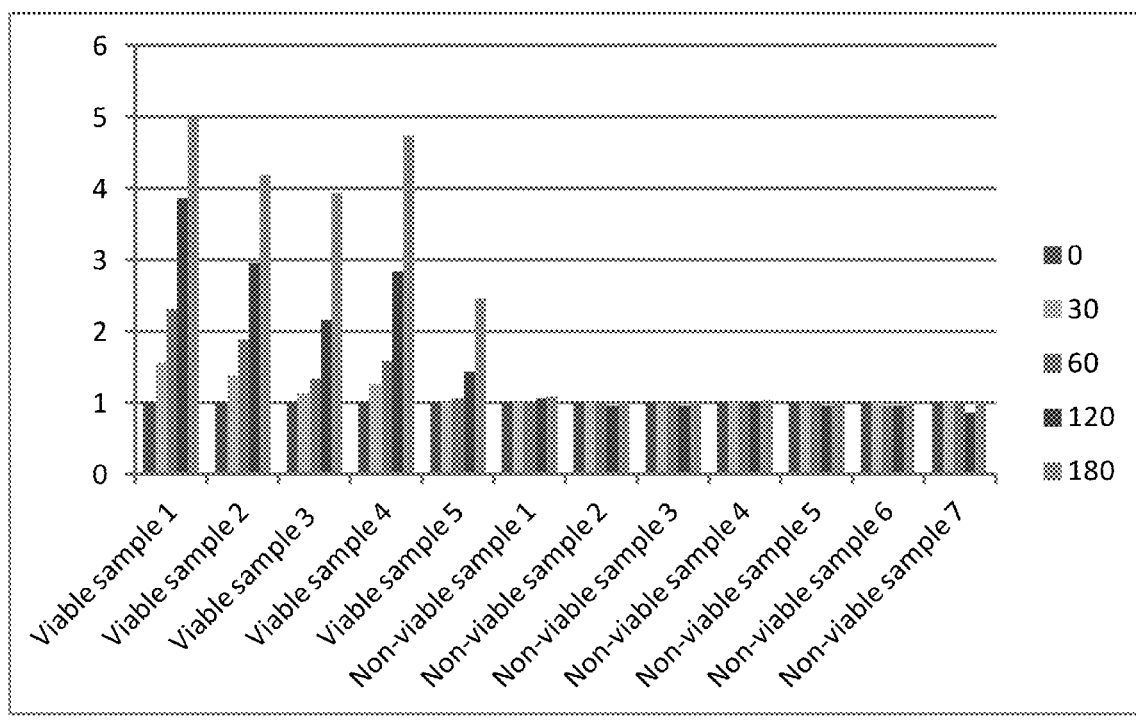
FIG. 12 is a graph which shows a comparison between the signal measured when spores survive the sterilization process with the signal measured when spores do not survive the sterilization process.

Twelve self-contained biological indicators containing *Geobacillus stearothermophilus* at a population of $2 \times 10^7$ CPU per SCSI are placed within a simulated use medical device load and are processed in an aborted (i.e., incomplete) cycle with a full load in a steam sterilizer. At the completion of the aborted cycles, the samples are removed and incubated at 56° C. for three hours. Samples are evaluated for the level of glucose in their media. FIG. 12 is a graph which shows a comparison between the signal measured when spores survive the sterilization process with the signal measured when spores do not survive the sterilization process.

Example 4

The detection of *Geobacillus stearothermophilus* spores at a population of 2E6 and supplemented with a-glucosidase at concentrations ranging from 0.4 units/ml to 9.7 units/ml was monitored using commercially available glucose strips and a commercially available glucose monitor. Incubation is performed in 500 μl of ½× glucose-free TSB with 4.5 g/l maltose and 5.5 g/l maltose at 56° C. for 4 hours. The glucose concentration of each sample is measured every hour by dipping a glucose strip into the growth media and taking a reading with the glucometer. Tables 2 and 3 show the results of the study for the growth media containing 4.5 g/l maltose and 5.5 g/l maltose, respectively. Any glucose reading above a "low" reading on the glucose meter indicates viable organisms are present in the solution. All data indicates that viable organisms can be detected in under an hour. Increasing numbers in the table indicate that more glucose molecules are being generated.

TABLE 2

Results of glucose readings for samples containing 4.5 g/l maltose

| | 1/2X Glucose-free TSB + 4.5 g/l maltose in *G. stearothermophilus* | | | | |
|---|---|---|---|---|---|
| Time (min) | Control - no maltose | 9.7 unit/ml enzyme | 4.9 units/ml enzyme | 0.9 units/ml enzyme | 0.4 units/ml enzyme |
| 0   | ER4 | Lo  | Lo  | Lo  | Lo |
| 60  | ER4 | 425 | 247 | 44  | 36 |
| 120 | ER4 | 455 | 346 | 81  | 54 |
| 180 | ER4 | 424 | 358 | 101 | 74 |
| 240 | ER4 | 440 | 425 | 143 | 99 |

TABLE 3

Results of glucose readings for samples containing 5.5 g/l maltose

| | 1/2X Glucose-free TSB + 5.5 g/l maltose in *G. stearothermophilus* | | | | |
|---|---|---|---|---|---|
| Time (min) | Control - no maltose | 9.7 unit/ml enzyme | 4.9 units/ml enzyme | 0.9 units/ml enzyme | 0.4 units/ml enzyme |
| 0   | ER4 | Lo  | Lo  | Lo  | Lo |
| 60  | ER4 | 457 | 287 | 51  | 38 |
| 120 | ER4 | 447 | 389 | 99  | 66 |
| 180 | ER4 | 440 | 433 | 127 | 90 |
| 240 | ER4 | 473 | 429 | 147 | 98 |

In the present invention the detection of viable organisms is performed through the monitoring of an electronic signal resulting from the breakdown of complex sugars into simple sugars in a coupled enzymatic reaction in which one of the enzymes is selected from those already produced by the indicator spore and the other from a set of simple sugar, e.g., glucose, reactive enzymes supplied as a component of the disclosed system in accordance with the invention. The examples cited herein show the demonstrated use of alpha glucosidase (naturally occurring and found in many strains of both *Geobacillus stearothermophilus* and *Bacillus atrophaeus*) and maltose (a disaccharide comprising two molecules of glucose). This embodiment is of particular interest because the starting material (maltose) does not interact with the ingredients to produce a signal without interaction with viable spores expressing active glucosidase. Maltose also provides two molecules of glucose rather than one which is the case for many other potential sugars like lactose. One could use other naturally occurring enzymes from the spore, for example, a galactosidase and a corresponding substrate like lactose (produces one glucose molecule and one galactose molecule) to achieve the same end—increasing the presence of a simple sugar, such as glucose, in the test solution. In either case, the product of the first step, a simple sugar (e.g., glucose) would interact with the enzyme of the cited example (e.g., glucose oxidase) to produce reaction products (e.g., hydrogen peroxide) and the detectable electron transfer of the present invention. As in the first step, alternative enzymes can be used in place of glucose oxidase, as for example glucose dehydrogenase, which also produces detectable electrons. The combination of these features represents a novel and quite unexpected system and method for determining the efficacy of a sterilization process. What is also novel and quite unexpected is the use of a hand-held glucose meter for the detection and evaluation of results leading to a PASS or FAIL designation based on detection of any remaining viable indicator spores. The system and method of the present invention thus may allow for read times as low as seconds to minutes, which is also novel and quite unexpected in the field of sterilization cycle monitoring.

While the principles of the invention have been explained in relation to certain particular embodiments, these embodiments are provided for purposes of illustration. It is to be understood that various modifications thereof will become apparent to those skilled in the art upon reading the specification. Therefore, it is to be understood that the invention disclosed herein is intended to cover such modifications as fall within the scope of the appended claims. The scope of the invention is limited only by the scope of the claims.

The invention claimed is:

1. A sterilization indicator system, comprising:
   a vial comprising:
      a first compartment comprising spores of one or more species of microorganism;
      a second compartment comprising a growth medium comprising one or more of a disaccharide, an oligosaccharide or a polysaccharide capable of conversion to a monosaccharide by germinating cells of the one or more species of microorganism, and
      wherein the vial is free of the monosaccharide and is adapted to combine contents of the first compartment with contents of the second compartment for incubation after the vial has been exposed to a sterilant;
   an enzyme, capable of acting upon the monosaccharide and producing an electron transfer, disposed on two or more electrodes adapted to carry an electrical signal resulting from the electron transfer when the enzyme acts upon the monosaccharide, wherein the pair of electrodes are positioned to contact the combined contents of the first compartment and the second compartment during and/or after incubation; and
   an apparatus linked or linkable to the electrodes and adapted to detect and measure the electrical signal resulting from the electron transfer when the enzyme acts upon the monosaccharide.

2. The sterilization indicator system of claim 1 wherein the one or more species of microorganism comprises one or both of *Geobacillus stearothermophilus* and *Bacillus atrophaeus*.

3. The sterilization indicator system of claim 1 wherein the disaccharide is maltose and the monosaccharide is glucose.

4. The sterilization indicator system of claim 1 wherein the disaccharide is maltose that is converted to glucose by a glucosidase produced by or present in the germinating cells during incubation of the combined contents of the first compartment and the second compartment.

5. The sterilization indicator system of claim 1 wherein the enzyme is provided together with one or more mediator.

6. The sterilization indicator system of claim 5 wherein the one or more mediator comprises one or a mixture of two or more of ferrocene, vinyl ferrocene, 1,1'-dimethyl ferrocene, carboxyferrocene, 1,1'-dicarboxy ferrocene, (dimethylamino)methyl ferrocene or ferrocyanide.

7. The sterilization indicator system of claim 1 wherein the at least two electrodes comprise graphite, graphene, carbon, carbon nanotubes, gold, platinum, palladium, silver, nickel or copper or a combination or alloy of any two or more thereof.

8. The sterilization indicator system of claim 1 wherein the enzyme is glucose oxidase.

9. The sterilization indicator system of claim 1 wherein the enzyme is glucose dehydrogenase.

10. A method of determining the efficacy of a sterilization process, comprising:
    providing the sterilization indicator system of claim 1;
    exposing the sterilization indicator to a sterilization process intended to kill the spores of the one or more species of microorganism;
    combining the contents of the first compartment and the second compartment;
    exposing the combined contents to the enzyme disposed on the two or more electrodes while incubating the combined contents;
    with the apparatus linked to the electrodes, detecting and measuring any electrical signal resulting from electron transfer when the enzyme acts upon the monosaccharide; and
    determining whether the sterilization process was efficacious.

11. The method of claim 10 wherein the one or more species of microorganism comprises one or both of *Geobacillus stearothermophilus* and *Bacillus atrophaeus*.

12. The method of claim 10 wherein the disaccharide is maltose and the monosaccharide is glucose.

13. The method of claim 10 wherein the disaccharide is maltose that is converted to glucose by a glucosidase produced by or present in the germinating cells during incubation of the combined contents of the first compartment and the second compartment.

14. The method of claim 10 wherein the enzyme is provided together with one or more mediator.

15. The method of claim 14 wherein the one or more mediator comprises one or a mixture of two or more of ferrocene, vinyl ferrocene, 1,1'-dimethyl ferrocene, carboxyferrocene, 1,1'-dicarboxy ferrocene, (dimethylamino)methyl ferrocene or ferrocyanide.

16. The method of claim 10 wherein the at least two electrodes comprise graphite, graphene, carbon, carbon nanotubes, gold, platinum, palladium, silver, nickel or copper or a combination or alloy of any two or more thereof.

17. The method of claim 10 wherein the enzyme is glucose oxidase.

18. The method of claim 10 wherein the enzyme is glucose dehydrogenase.